US00PP23414P2

(12) United States Plant Patent
MacKenzie

(10) Patent No.: US PP23,414 P2
(45) Date of Patent: Feb. 19, 2013

(54) ***SEDUM* PLANT NAMED 'NONAG'**

(50) Latin Name: ***Sedum kamtschaticum* var. *floriferum***
Varietal Denomination: Nonag

(75) Inventor: David MacKenzie, Nunica, MI (US)

(73) Assignee: Hortech, Inc., Spring Lake, MI (US)

( * ) Notice: Subject to any disclaimer, the term of this patent is extended or adjusted under 35 U.S.C. 154(b) by 0 days.

(21) Appl. No.: 13/200,885

(22) Filed: Oct. 4, 2011

(51) Int. Cl.
*A01H 5/00* (2006.01)

(52) U.S. Cl. ..... Plt./479

(58) Field of Classification Search ..... Plt./479
See application file for complete search history.

*Primary Examiner* — Kent L Bell
(74) *Attorney, Agent, or Firm* — Penny J. Aguirre

(57) ABSTRACT

A new cultivar of *Sedum* plant, 'Nonag', characterized by its glossy foliage that emerges shiny green in color, holding this color during summer, then changing to a mahogany color during fall and winter, its green stems, its flowers in late spring and early summer that are bright lemon yellow and held upon rounded somewhat drooping inflorescences atop a dense, low growing plant habit.

1 Drawing Sheet

Botanical classification: *Sedum kamtschaticum* var. *floriferum.*

Variety denomination: 'Nonag'.

CROSS REFERENCE TO RELATED APPLICATIONS

This application is co-pending with a U.S. Plant Patent Applications by the same Inventory and pertain to plants derived from the same parentage, the applications are entitled *Sedum* Plant named 'Nonof' (U.S. Plant patent application Ser. No. 13/200,871), and *Sedum* Plant named 'Nonel' (U.S. Plant patent application Ser. No. 13/200,893).

BACKGROUND OF THE INVENTION

The present invention relates to a new and distinct cultivar of *Sedum* plant, botanically known as *Sedum kamtschaticum* var. *floriferum* 'Nonag' and will be referred to hereinafter by its cultivar name, 'Nonag'. The new cultivar of *Sedum* is a hardy herbaceous perennial grown for use as a landscape and container plant and is particularly suitable as a ground cover.

'Nonag' was discovered in March of 2009 as a naturally occurring whole plant mutation in the Inventor's nursery in Nunica, Mich. as a single unique plant in a field planted with 50,000 seedlings from unnamed plants of *Sedum kamtschaticum* var. *floriferum.*

Asexual reproduction of the new cultivar was first accomplished by stem cuttings in June of 2009 in Nunica, Mich. Propagation by cuttings and crown division has determined the characteristics to be stable and reproduced true to type in successive generations.

SUMMARY OF THE INVENTION

The following traits have been repeatedly observed and are determined to be the characteristics of the new cultivar. These attributes in combination distinguish 'Nonag' as a unique cultivar of *Sedum.*

1. 'Nonag' exhibits foliage that emerges shiny green and stays shiny green throughout summer, then turns a distinct mahogany color during fall, and winter.

2. 'Nonag' exhibits flower buds that are bright yellow.
3. 'Nonag' exhibits numerous, rounded, somewhat drooping inflorescences with flowers of bright lemon yellow during early summer.
4. 'Nonag' exhibits a dense, low growing habit with foliage that reaches 6 to 7 inches in height.

The exact parent plant of 'Nonag' is unknown, however the plants in the field block *Sedum kamtschaticum* var. *floriferum* in which 'Nonel' was discovered has foliage that reached 5 inches in height and foliage that is maroon in color during the fall and winter months. 'Nonel' can be compared to other cultivars of *Sedum kamtschaticum* var. *floriferum* (all unpatented) which differ from 'Nonel' in the following characteristics; 'Czar's Gold' differs in having red stems, shorter and broader foliage, a mature height of 5 inches, and sparsely borne rounded inflorescences; 'Weihenstephaner Gold' differs in having red stems, and narrower and longer foliage which turns bronze during the fall and winter months.

'Nonag' can be compared to other cultivars selected from the same field of seedlings; 'Nonof' and 'Nonel'. 'Nonof' differs from 'Nonag' in having foliage that in shiny green and remains shiny green in the fall and winter and in reaching 4.5 inches in height. 'Nonel' differs from 'Nonag' in having foliages that turns deep red-purple during fall and winter and reaches 4 inches in height.

BRIEF DESCRIPTION OF THE DRAWINGS

The accompanying colored photograph illustrates the overall appearance and distinct characteristics of the new *Sedum*. The photograph was taken of a 2 year-old plants of 'Nonag' as grown in the ground in full sun in Nunica, Mich.

The photograph in FIG. 1 illustrates the unique foliage coloration of 'Nonag'.

The colors in the photographs may differ slightly from the color values cited in the detailed botanical description, which accurately describe the colors of the new *Sedum.*

DETAILED BOTANICAL DESCRIPTION

The following is a detailed description of the new cultivar as observed on 2 year-old plants of 'Nonag' as grown in the ground in full sun in Nunica, Mich. The phenotype of the new cultivar may vary with variations in environmental, climatic, and cultural conditions, as it has not been tested under all possible environmental conditions. The color determination is in accordance with The 2001 R.H.S. Colour chart of The Royal Horticultural Society, London, England, except where general color terms of ordinary dictionary significance are used.

General description:

*Blooming period.*—The last two weeks of June to the first or second week of July in Michigan.

*Plant habit.*—Herbaceous perennial, dense, low growing habit, mature plant sprawl from central crown with procumbent stems rooting as they contact the ground.

*Height and spread.*—Reaches 6 to 7 inches in height (foliage) and 7.5 inches in bloom, maximum spread is about 2 feet.

*Hardiness.*—Reliably in U.S.D.A. Zones 4B to 7B.

*Disease and pests.*—No susceptibility or resistance to diseases or pests has been observed.

*Propagation.*—Stem cuttings spring through summer and crown division throughout the year.

*Roots.*—Fibrous.

*Growth rate.*—Moderate.

Stem description:

*Stem shape.*—Round.

*Stem size.*—6 to 7 inches in length and about ⅛ inch in width.

*Internode length.*—An average of ⅛ inch.

*Stem color.*—147B.

*Stem surface.*—Glabrous.

*Branching habit.*—Sparsely branched.

Foliage description:

*Leaf shape.*—Acicular.

*Leaf division.*—Simple.

*Leaf arrangement.*—Alternate.

*Leaf base.*—Truncate.

*Leaf apex.*—Acute.

*Leaf venation.*—Not conspicuous, color matched leaf color.

*Leaf margins.*—Smooth, young leaves papilose-ciliate.

*Leaf attachment.*—Sessile.

*Leaf presence and orientation.*—Ascending.

*Leaf surface.*—Glabrous and waxy on upper and lower surface.

*Leaf color.*—Young and mature leaves 144B on upper and lower surface, fall leaves upper and lower surface 178A.

*Leaf size.*—Young leaves; an average of ¼ inch in length and 1/16 inch in width, mature leaves; an average of ¾ inches in length and ⅛ inch in width.

Flower description:

*Inflorescence type.*—Terminal, cymose, drooping and sub-globose in bud, erect and flat in flower, concave in fruit, branches short and forked, dense, many flowered, sparingly leafy.

*Inflorescence size.*—An average of 2 inches in width and 2½ inches in depth.

*Lastingness of inflorescence.*—About one month.

*Flower type.*—Perfect, spreading, 5-starred.

*Flower number.*—25 to 30 flowers per cyme.

*Flower fragrance.*—None.

*Flower buds.*—Conical in shape, about ¼ inch in length and ⅛ inch in diameter, ribbed surface, 7A in color.

*Flower size.*—About ¼ inch in depth and ⅜ inch in diameter.

*Peduncles.*—Round, an average of ½ inch in length and ⅛ inch in width, 186C in color, glabrous surface.

*Pedicels.*—Round, range from ⅛ to ¼ inch in length, 1/16 inch in width, 144B in color, glabrous surface.

*Sepals.*—5, spreading, ovate to lanceolate in shape, about ⅛ inch in length and 1/16 inch in width, 145B in color on both surfaces, entire margin, acute apex, truncate base, glabrous on both surfaces.

*Petals.*—5, spreading, lanceolate in shape, truncate base, acute apex, entire margin, color of inner and outer surfaces is 7A, glabrous on both surfaces.

Reproductive organs:

*Pistils.*—5, held erect, about ⅜ inch in length, stigma irregularly globose in shape, 1/32 inch in width and 154B in color, styles lanceolate in shape, ¼ inch in length and 154D in color, ovary 1/10 inch in diameter and 151B in color.

*Stamens.*—10, about ⅛ inch in length, filament 151D in color, anther conical in shape, 1/16 inch in length, 151C in color, pollen is sparse in quantity and 151D in color.

*Fruit.*—Rounded with pointed tip, aggregate, range from 1/16 to ⅛ inch in length and ¼ inch in width, 151D in color, seed production was not observed.

It is claimed:

1. A new and distinct variety of *Sedum* plant named 'Nonag' as described and illustrated herein.

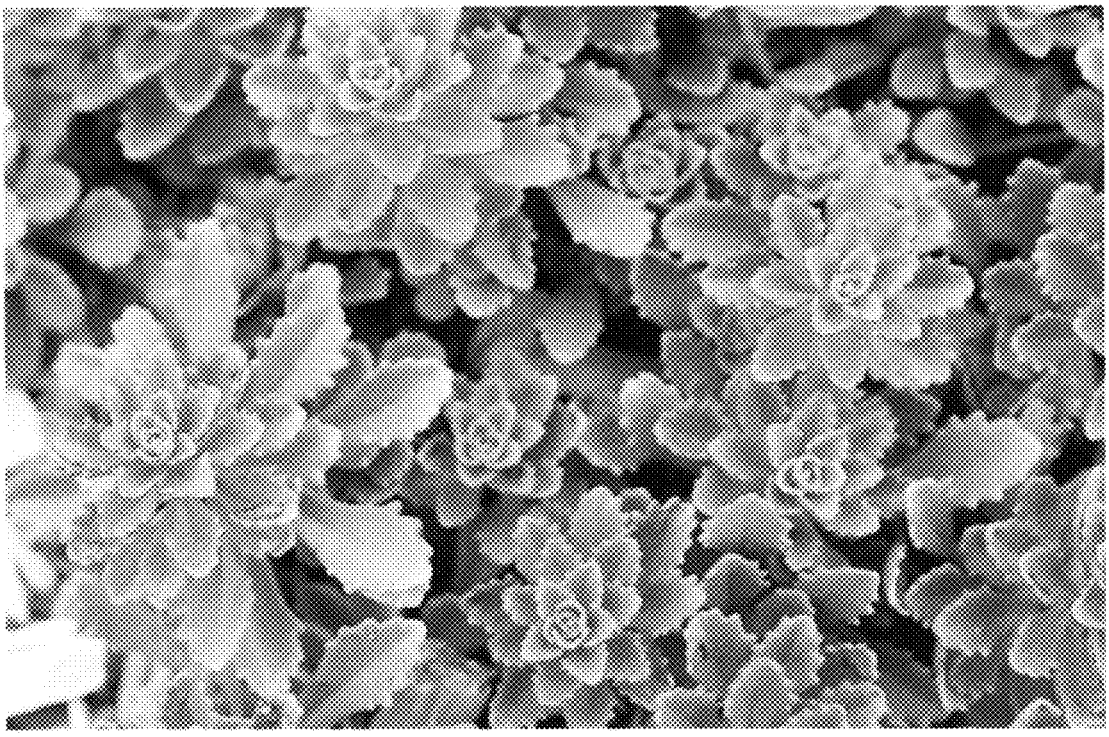

* * * * *